United States Patent

Kraatz et al.

Patent Number: 5,047,415

Date of Patent: * Sep. 10, 1991

[54] 2,2-DIHALOGENOCYCLOPROPYL-HYDROXY-ETHYLTRIAZOLES

[75] Inventors: Udo Kraatz, Leverkusen; Graham Holmwood, Wupertal; Karl-Rudolf Gassen, Odenthal; Stefan Dutzmann, Duesseldorf; Wilhelm Brandes, Leichlingen, all of Fed. Rep. of Germany

[73] Assignee: Bayer Aktiengesellschaft, Leverkusen, Fed. Rep. of Germany

[*] Notice: The portion of the term of this patent subsequent to Jun. 18, 2008 has been disclaimed.

[21] Appl. No.: 378,730

[22] Filed: Jul. 12, 1989

[30] Foreign Application Priority Data

Jul. 19, 1988 [DE] Fed. Rep. of Germany ....... 3824435

[51] Int. Cl.$^5$ ................ A01N 43/653; C07D 249/08
[52] U.S. Cl. ................ 514/383; 548/267.8; 548/268.6
[58] Field of Search ............ 548/101, 262, 267.8, 548/268.6; 514/184, 383

[56] References Cited

U.S. PATENT DOCUMENTS

| | | | |
|---|---|---|---|
| 4,507,140 | 3/1985 | Sugavanam | 514/383 |
| 4,734,126 | 3/1988 | Holmwood et al. | 548/262 |
| 4,847,278 | 7/1989 | Kramer et al. | 548/262 |

FOREIGN PATENT DOCUMENTS 2129000  5/1984  United Kingdom ........ 548/262

OTHER PUBLICATIONS

Mueller et al., "Microficidal and Plant, etc." CA100:85702n (1984).

Primary Examiner—Mary C. Lee
Assistant Examiner—Patricia L. Morris
Attorney, Agent, or Firm—Sprung, Horn, Kramer & Woods

[57] ABSTRACT

Novel 2,2-dihalogenocyclopropyl-hydroxy-ethyltriazoles of the formula

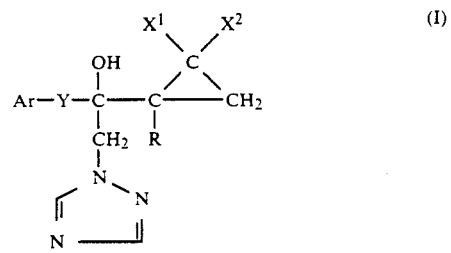

in which
Ar represents optionally substituted aryl,
R represents alkyl, optionally substituted aryl or optionally substituted aralkyl,
$X^1$ represents halogen,
$X^2$ represents halogen and p0 Y represents the groups —OCH$_2$—, —SCH$_2$—, —CH$_2$CH$_2$— or —CH=CH—, where the hetero atom is linked to the aryl radical when Y represents —OCH$_2$— or —SCH$_2$—, and acid addition salts or metal salt complexes thereof, are fungicidally active.

7 Claims, No Drawings

2,2-DIHALOGENOCYCLOPROPYL-HYDROXY-ETHYLTRIAZOLES

The present invention relates to novel 2,2-dihalogenocyclopropyl-hydroxy-ethyltriazoles, a process for the preparation thereof, and their use as fungicides.

It has already been disclosed that certain cyclopropyl-hydroxy-ethyltriazoles possess fungicidal properties (cf. EP-OS (European Published Specification) 0,040,345 and EP-OS (European Published Specification) 0,180,136). Thus, for example, 1-(4-chlorophenoxy)-2-cyclopropyl-3-(1,2,4-triazol-1-yl)-propan-2-ol, 1-(4-chlorophenyl)-1-(1-chloro-cycloprop-1-yl)-2-(1,2,4-triazol-1-yl)-ethan-1-ol and 1-(4-chlorophenyl)-1-[1-(2,4-dichlorophenoxy)-cycloprop-1-yl]-ethan-1-ol can be used for combating fungi. The activity of these substances is good but in some cases leaves something to be desired when low application rates are used.

Novel 2,2-dihalogenocyclopropyl-hydroxy-ethyltriazoles of the formula

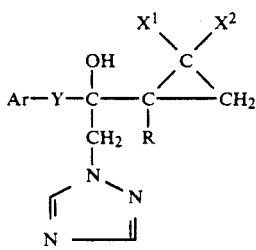

in which
Ar represents optionally substituted aryl,
R represents alkyl, optionally substituted aryl or optionally substituted aralkyl,
$X^1$ represents halogen,
$X^2$ represents halogen and
Y represents the groups —OCH$_2$—, —SCH$_2$—, —CH$_2$CH$_2$— or —CH=CH—, where the hetero atom is linked to the aryl radical when Y represents —OCH$_2$— or —SCH$_2$—,
and acid addition salts and metal salt complexes thereof have now been found.

The substances according to the invention contain an asymmetrically substituted carbon atom. They can thus be obtained in the form of optical isomers. Moreover, those substances of the formula (I) in which Y represents a —CH=CH— group can also be present in the form of E- or Z-isomers. The invention relates both to the individual isomers and to their mixtures.

Furthermore, it has been found that 2,2-dihalogenocyclopropyl-hydroxy-ethyltriazoles of the formula (I) and acid addition salts and metal salt complexes thereof are obtained when oxiranes of the formula

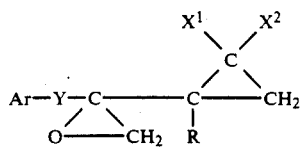

in which Ar, R, $X^1$, $X^2$ and Y have the abovementioned meanings, are reacted with 1,2,4-triazole of the formula

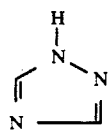

in the presence of an acid-binding agent and in the presence of a diluent and, if appropriate, an acid or a metal salt are subsequently added onto the resultant compounds of the formula (I).

Finally, it has been found that the novel 2,2-dihalogenocyclopropyl-hydroxy-ethyltriazoles of the formula (I) and the acid addition salts and metal salt complexes thereof possess powerful fungicidal properties.

Surprisingly, the substances according to the invention show a better fungicidal activity than 1-(4-chlorophenoxy)-2-cyclopropyl-3-(1,2,4-triazol-1-yl)propan-2-ol, 1-(4-chlorophenyl)-1-(1-chloro-cycloprop-1-yl)-2-(1,2,4-triazol-1-yl)-ethan-1-ol and 1-(4-chlorophenyl)-1-[1-(2,4-dichlorophenoxy)-cycloprop-1-yl]-ethan-1-ol, which are previously known compounds of a similar structure and of the same direction of action.

Formula (I) provides a general definition of the 2,2-dihalogenocyclopropyl-hydroxy-ethyltriazoles according to the invention. In this formula, Ar preferably represents phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and is optionally substituted by alkyl having 1 or 2 carbon atoms and/or halogen, phenyl which is optionally substituted by alkyl having 1 or 2 carbon atoms and/or halogen or phenoxy which is optionally substituted by alkyl having 1 or 2 carbon atoms and/or halogen, preferably represents alkyl having 1 to 4 carbon atoms, for phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinomethyl having 1 to 4 carbon atoms in the alkyl moiety and 1 to 4 carbon atoms in the alkoxy moiety, phenoximinoalkyl which has 1 to 4 carbon atoms in the alkyl moiety and is optionally substituted by alkyl having 1 or 2 carbon atoms and/or halogen, phenyl which is optionally substituted by alkyl having 1 or 2 carbon atoms and/or halogen, or by phenoxy which is optionally substituted by alkyl having 1 or 2 carbon atoms and/or halogen, or for benzyl which can be monosubstituted to trisubstituted in the phenyl moiety by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and is optionally substituted by alkyl having 1 or 2 carbon atoms and/or halogen, or by phenyl which is optionally substituted by alkyl having 1 or 2 carbon atoms and/or halogen, or by phenoxy which is optionally substituted by alkyl having 1 or 2 carbon atoms and/or halogen, $X^1$ preferably represents fluorine, chlorine or bromine, $X^2$ preferably represents fluorine, chlorine or bromine and Y preferably represents the groups —OCH$_2$—, —SCH$_2$—, —CH$_2$CH$_2$— or —CH=CH—, where the hetero atom is linked to the aryl radicals when Y represents —OCH$_2$— or —SCH$_2$—.

Particularly preferred compounds of the formula (I) are those in which

Ar represents phenyl which can be monosubstituted to trisubstituted by identical or different substituents from the series comprising fluorine, chlorine, bromine, methyl, ethyl, isopropyl, tert.-butyl, methoxy, methylthio, trifluoromethyl, trifluoromethoxy, trifluoromethylthio, methoximinomethyl, 1-methoximino-1-ethyl, ethoximinomethyl, phenyl which is optionally substituted by fluorine, chlorine and/or methyl, or by phenoxy which is optionally substituted by fluorine, chlorine and/or methyl;

R represents methyl, ethyl, isopropyl, tert.-butyl or phenyl which is optionally monosubstituted to disubstituted by identical or different substituents from the series comprising fluorine, chlorine or methyl, or represents benzyl which can be monosubstituted or disubstituted in the phenyl moiety by identical or different substituents from the series comprising fluorine, chlorine and/or methyl, $X^1$ represents fluorine or chlorine, $X^2$ represents fluorine or chlorine and Y represents the groups —OCH$_2$—, —SCH$_2$—, —CH$_2$CH$_2$— or —CH=CH—, where the hetero atom is linked to the aryl radical when Y represents —OCH$_2$— or —SCH$_2$—.

Very particularly preferred compounds of the formula (I) are those in which

Ar represents phenyl which can be monosubstituted to trisubstituted by identical or different substituents from the series comprising fluorine, chlorine, bromine, methyl, ethyl, isopropyl, tert.-butyl, methoxy, methylthio, trifluoromethyl, trifluoromethoxy, trifluoromethylthio, methoximinomethyl, 1-methoximino-1-ethyl, ethoximinomethyl, phenyl which is optionally substituted by fluorine, chlorine and/or methyl or by phenoxy which is optionally substituted by fluorine, chlorine and/or methyl, R represents methyl, ethyl, phenyl which is optionally monosubstituted or disubstituted by fluorine, chlorine and/or methyl, or for benzyl, $X^1$ represents fluorine or chlorine, $X^2$ represents fluorine or chlorine and Y represents the group —OCH$_2$—, —SCH$_2$—, —CH$_2$CH$_2$— or —CH=CH—, where the hetero atom is linked to the aryl radical when Y represents —OCH$_2$— or —SCH$_2$—.

Other preferred compounds according to the invention are addition products of acids and those 2,2-dihalogenocyclopropyl-hydroxy-ethyltriazoles of the formula (I) in which Ar, R, $X^1$, $X^2$ and Y have the meanings which have already been mentioned as being preferred for these radicals.

The acids which can be added on preferably include hydrohalic acids, such as, for example, hydrochloric acid and hydrobromic acid, in particular hydrochloric acid, furthermore phosphoric acid, nitric acid, sulphuric acid, mono- and bi-functional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid, 1,5-naphthalenedisulphonic acid or camphorsulphonic acid.

Other preferred compounds according to the invention are addition products of salts of metals of main groups II to IV and of subgroups I and II and IV to VIII of the periodic table of the elements and those 2,2-dihalogenocyclopropyl-hydroxy-ethyltriazoles of the formula (I) in which Ar, R, $X^1$, $X^2$ and Y have the meanings which have already been mentioned as being preferred for these radicals.

In this context, the salts of copper, zinc, manganese, magnesium, tin, iron and of nickel are particularly preferred. Suitable anions of these salts are those which are derived from those acids which lead to physiologically tolerable addition products.

In this connection, particularly preferred acids of this type are the hydrohalic acids, such as, for example, hydrochloric acid and hydrobromic acid, furthermore phosphoric acid, nitric acid and sulphuric acid.

The substances listed in the table below may be mentioned as examples of 2,2-dihalogenocyclopropyl-hydroxy-ethyltriazoles of the formula (I):

TABLE 1

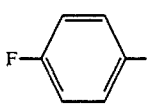

| Ar | Y | R | $X^1$ | $X^2$ |
|---|---|---|---|---|
| F—⟨phenyl⟩— | —OCH$_2$— | CH$_3$ | F | F |

TABLE 1-continued (I)

$$Ar-\underset{\underset{\underset{N\diagdown \diagup N}{\overset{|}{CH_2}}}{\overset{OH}{|}}}{C}-\underset{\underset{R}{\overset{|}{C}}}{\overset{X^1}{\overset{|}{C}}}\overset{X^2}{\underset{CH_2}{\diagdown}}$$

| Ar | Y | R | X¹ | X² |
|---|---|---|---|---|
| 2-Cl-C₆H₄ | —OCH₂— | CH₃ | F | F |
| 4-(H₃CON=CH)-C₆H₄ | —OCH₂— | CH₃ | F | F |
| 4-F₃C-C₆H₄ | —OCH₂— | CH₃ | F | F |
| 3-Cl-C₆H₄ | —OCH₂— | CH₃ | F | F |
| 4-H₃CO-C₆H₄ | —OCH₂— | CH₃ | F | F |
| 4-H₃CS-C₆H₄ | —OCH₂— | CH₃ | F | F |
| 4-H₃C-C₆H₄ | —OCH₂— | CH₃ | F | F |
| 2,4,5-Cl₃-C₆H₂ | —OCH₂— | CH₃ | F | F |
| 4-C₆H₅-C₆H₄ | —OCH₂— | CH₃ | F | F |
| 4-C₆H₅O-C₆H₄ | —OCH₂— | CH₃ | F | F |
| 2-F-C₆H₄ | —OCH₂— | CH₃ | F | F |
| 4-Cl-C₆H₄ | —SCH₂— | CH₃ | F | F |
| 4-F₃CO-C₆H₄ | —SCH₂— | CH₃ | F | F |
| 2,4-Cl₂-C₆H₃ | —SCH₂— | CH₃ | F | F |
| 2-CH₃-4-Cl-C₆H₃ | —SCH₂— | CH₃ | F | F |
| 2,4-F₂-C₆H₃ | —SCH₂— | CH₃ | F | F |
| 4-F-C₆H₄ | —SCH₂— | CH₃ | F | F |
| 2-Cl-C₆H₄ | —SCH₂— | CH₃ | F | F |
| 4-(H₃CON=CH)-C₆H₄ | —SCH₂— | CH₃ | F | F |
| 4-F₃C-C₆H₄ | —SCH₂— | CH₃ | F | F |

TABLE 1-continued $$\text{Ar} - Y - \underset{\underset{CH_2}{|}}{\overset{\overset{OH}{|}}{C}} - \underset{R}{\overset{X^1}{\underset{|}{C}}} \overset{X^2}{\underset{CH_2}{\diagdown}}$$ (I)

$$\underset{N \diagdown\diagup N}{\overset{|}{N}}$$

| Ar | Y | R | $X^1$ | $X^2$ |
|---|---|---|---|---|
| 3-Cl-C₆H₄— | —SCH₂— | CH₃ | F | F |
| 4-H₃CO-C₆H₄— | —SCH₂— | CH₃ | F | F |
| 4-H₃CS-C₆H₄— | —SCH₂— | CH₃ | F | F |
| 4-H₃C-C₆H₄— | —SCH₂— | CH₃ | F | F |
| 2,4,5-Cl₃-C₆H₂— | —SCH₂— | CH₃ | F | F |
| 4-C₆H₅-C₆H₄— | —SCH₂— | CH₃ | F | F |
| 4-C₆H₅O-C₆H₄— | —SCH₂— | CH₃ | F | F |
| 2-F-C₆H₄— | —SCH₂— | CH₃ | F | F |
| 4-F₃CO-C₆H₄— | —CH₂CH₂— | CH₃ | F | F |
| 2,4-Cl₂-C₆H₃— | —CH₂CH₂— | CH₃ | F | F |
| 4-Cl-2-CH₃-C₆H₃— | —CH₂CH₂— | CH₃ | F | F |
| 2,4-F₂-C₆H₃— | —CH₂CH₂— | CH₃ | F | F |
| 4-F-C₆H₄— | —CH₂CH₂— | CH₃ | F | F |
| 2-Cl-C₆H₄— | —CH₂CH₂— | CH₃ | F | F |
| 4-(H₃CON=CH)-C₆H₄— | —CH₂CH₂— | CH₃ | F | F |
| 4-F₃C-C₆H₄— | —CH₂CH₂— | CH₃ | F | F |
| 3-Cl-C₆H₄— | —CH₂CH₂— | CH₃ | F | F |
| 4-H₃CO-C₆H₄— | —CH₂CH₂— | CH₃ | F | F |
| 4-H₃CS-C₆H₄— | —CH₂CH₂— | CH₃ | F | F |
| 4-H₃C-C₆H₄— | —CH₂CH₂— | CH₃ | F | F |

TABLE 1-continued
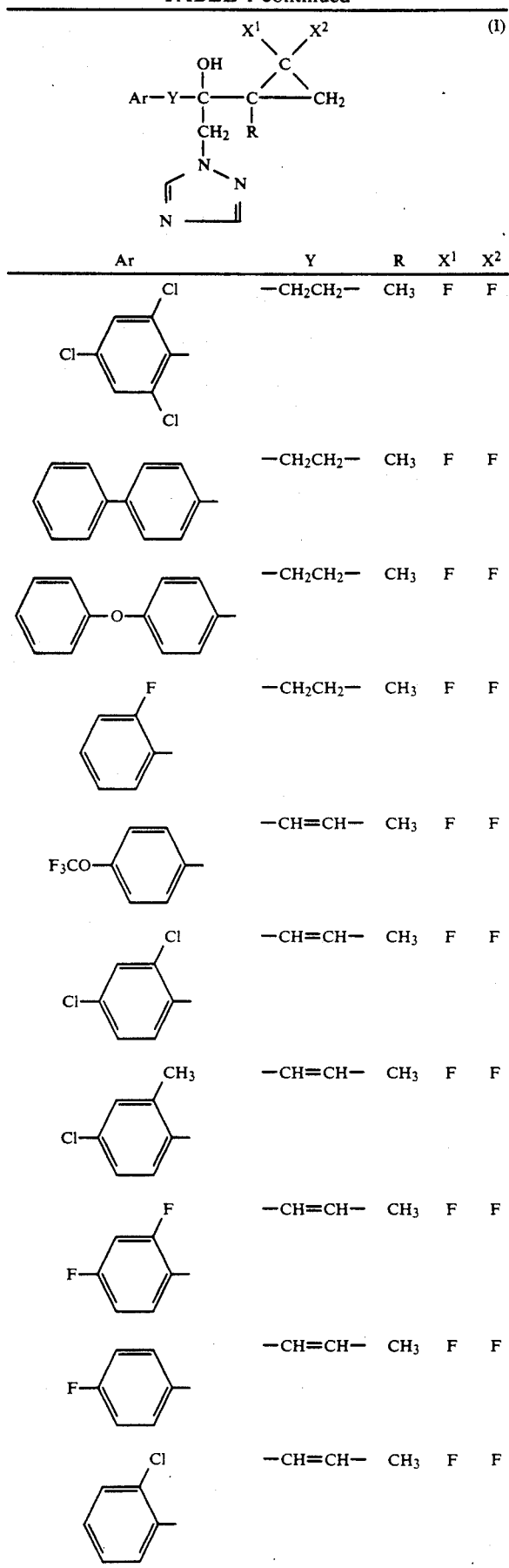
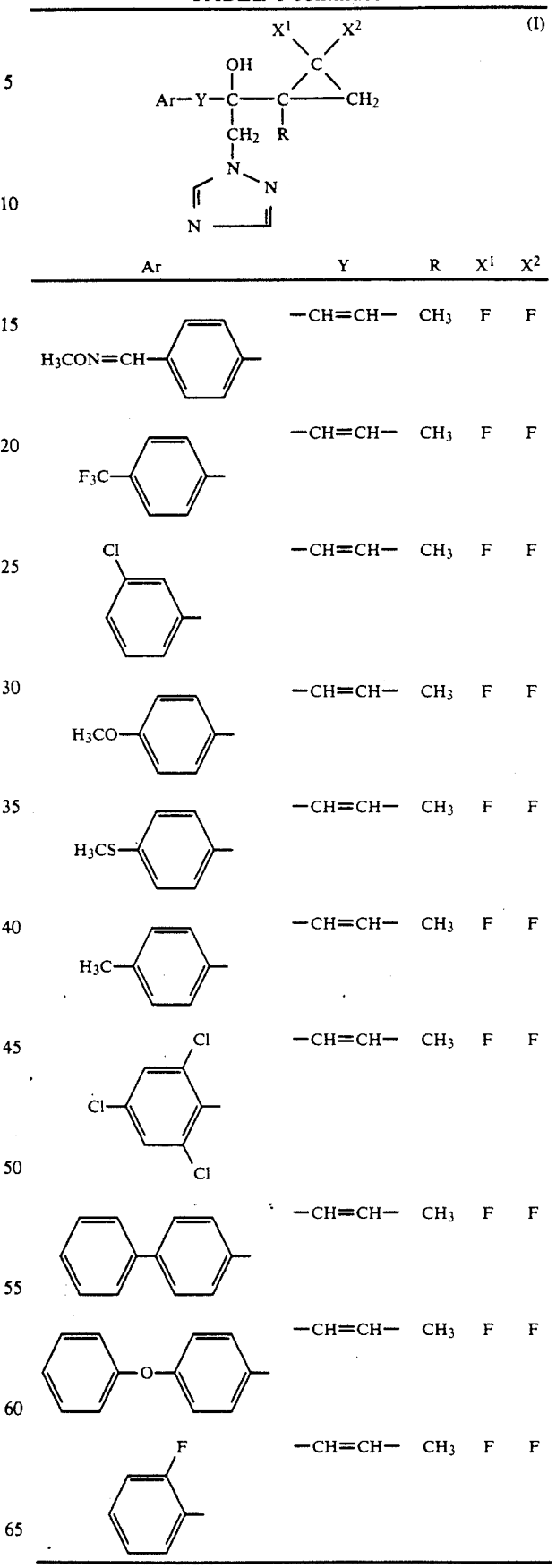

If 2-(4-chlorophenoxymethyl)-2-(2,2-difluoro-1-methylcyclopropyl)-oxirane and 1,2,4-triazole are used as starting substances, the course of the process according to the invention can be illustrated by the following equation:

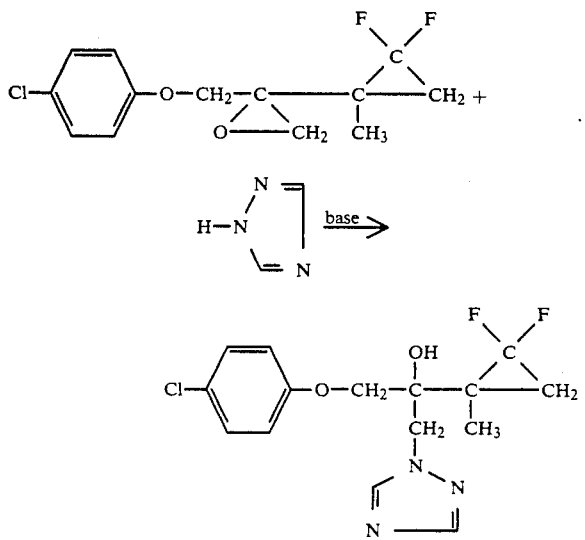

Formula (II) provides a general definition of the oxiranes required as starting substances in the process according to the invention. In this formula, Ar, R, $X^1$, $X^2$ and Y preferably have those meanings which have already been mentioned in connection with the description of the substances of the formula (I) according to the invention as being preferred for these radicals.

The oxiranes of the formula (II) were hitherto unknown. They can be prepared by a process in which a) cyclopropyl ketones of the formula

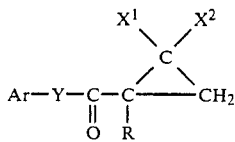 (IV)

in which Ar, R, $X^1$, $X^2$ and Y have the abovementioned meaning,
are reacted either
α) with dimethyloxosulphonium methylide of the formula

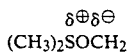 (V)

or
β) with dimethylsulphonium methylide of the formula

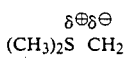 (VI)

in the presence of a diluent.

The cyclopropyl ketones of the formula (IV) required as starting substances for carrying out process (a) were hitherto unknown. They can be prepared by a process in which b) halogenoketones of the formula

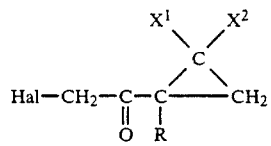 (VII)

in which
Hal represents chlorine or bromine and
R, $X^1$ and $X^2$ have the abovementioned meanings,
are reacted with compounds of the formula Ar—Z—H     (VIII)

in which
Ar has the abovementioned meaning and
Z represents oxygen or sulphur,
in the presence of an acid-binding agent and if appropriate in the presence of a diluent; or c) aldehydes of the formula Ar—CHO     (IX)

in which Ar has the abovementioned meaning,
are reacted with methyl cyclopropyl ketones of the formula

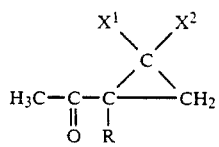 (X)

in which R, $X^1$ and $X^2$ have the abovementioned meanings,
in the presence of a catalyst and in the presence of a diluent and, if appropriate, the resultant cyclopropyl ketones of the formula

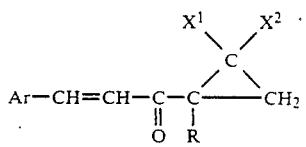 (XI)

in which Ar, R, $X^1$ and $X^2$ have the abovementioned meanings,
are hydrogenated in the presence of a catalyst and in the presence of a diluent.

The halogenoketones of the formula (VII) required as starting substances in process (b) were hitherto unknown. They can be prepared by a process in which d) methyl cyclopropyl ketones of the formula

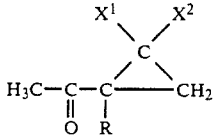 (X)

in which R, $X^1$ and $X^2$ have the abovementioned meanings,
are reacted with chlorinating agents or brominating agents in the presence of a diluent.

The ketones of the formula (X) required as starting substances in processes (c) and (d) were likewise hitherto unknown. They can be prepared by reacting vinylcyclopropane derivatives of the formula

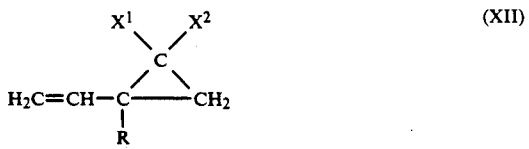

(XII)

in which R, $X^1$ and $X^2$ have the abovementioned meanings,
with strong oxidants, such as, for example, potassium permanganate, in the presence of a diluent, such as, for example, water, at temperatures between 0° C. and 30° C., and the resulting cyclopropanecarboxylic acids of the formula

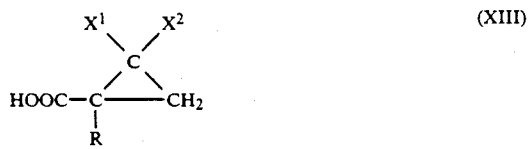

(XIII)

in which R, $X^1$ and $X^2$ have the abovementioned meanings,
are reacted with methyl-lithium in the presence of a diluent, such as, for example, diethyl ether, at temperatures between $-80°$ C. and $+20°$ C.

Some of the vinylcyclopropane derivatives of the formula (XII) are known (cf. Chem. Ber. 109, 2351 (1976)); or they can be prepared in a generally known manner, for example by addition of dihalogenocarbenes onto corresponding dienes.

Suitable chlorinating and brominating agents in process (d) are all chlorinating and brominating reagents which are customary for reactions of this type. Sulphuryl chloride, sulphuryl bromide and bromine can preferably be used.

Possible diluents in process (d) are all inert organic solvents which are customary for reactions of this type. Halogenated aliphatic hydrocarbons, such as methylene chloride, chloroform and carbon tetrachloride, can preferably be used.

The reaction temperatures in process (d) can be varied within a certain range. In general, the process is carried out at temperatures between $-10°$ C. and $+60°$ C., preferably between 0° C. and $+40°$ C.

Process (d) and likewise the other processes described in this application are generally carried out under atmospheric pressure. However, it is also possible in each case to carry out the process under increased or reduced pressure.

When carrying out process (d), a stoichiometric amount or alternatively a slight excess of chlorinating or brominating agent is generally employed per mole of ketone of the formula (X). Working up is carried out by customary methods. In general, a procedure is followed in which the reaction mixture is washed in succession with dilute aqueous sodium hydrogen carbonate solution and water, then dried and concentrated.

The aldehydes of the formula (IX) furthermore required as starting substances in process (c) are generally known compounds of organic chemistry.

Possible catalysts for carrying out step one of process (c) are all reaction accelerators which are customary for condensations of this type. Basic substances, for example alkali metal hydroxides, such as sodium hydroxide or potassium hydroxide, can preferably be used.

Suitable diluents for carrying out step one of process (c) are all inert organic solvents which are customary for reactions of this type. Alcohols, such as methanol, ethanol, isopropanol, n-butanol and tert.-butanol can preferably be used.

When carrying out step one of process (c), the reaction temperatures can be varied within a relatively wide range. In general, the process is carried out at temperatures between 0° C. and 100° C., preferably between 10° C. and 80° C.

Step one of process (c) is generally carried out under atmospheric pressure. However, it is also possible to carry out the process under increased or reduced pressure.

When carrying out step one of process (c), 1 mole of aldehyde of the formula (IX) and a catalytic amount of reaction accelerators are employed per mole of methyl cyclopropyl ketone of the formula (X). However, it is also possible to use an excess of one or the other component. Working up is carried out by customary methods. In general, a procedure is followed in which the reaction products obtained in the solid state are filtered off with suction and used for the further reactions, if appropriate with previous purification.

In step two of process (c), the cyclopropyl ketones of the formula (XI) are hydrogenated with hydrogen in the presence of a catalyst and of a diluent. This process is carried out in the liquid phase using a suspended, pulverulent hydrogenation catalyst (heterogeneous) or using a catalyst complex which is soluble in the diluent (homogeneous). The hydrogenation can be carried out discontinuously (batchwise) or continuously as bottom phase hydrogenation or hydrogenation with downward flow of the liquid phase in known hydrogenation reactors, such as autoclaves, autoclave cascades, tubular reactors or circulation reactors. The preferred way is the discontinuous bottom phase hydrogenation in an autoclave under increased pressure.

Suitable diluents for carrying out step two of process (c) are inert organic solvents. These preferably include alcohols, such as methanol, ethanol, isopropanol or ethylene glycol; ethers, such as diethyl ether, diisopropyl ether, ethylene glycol monomethyl ether, ethylene glycol dimethyl ether, dioxane or tetrahydrofuran; saturated hydrocarbons, such as n-heptane or cyclohexane; aromatic hydrocarbons, such as toluene; and also esters, such as ethyl acetate.

Suitable hydrogenation catalysts for step two of process (c) are for example those which consist of, or contain, metals and/or compounds of elements of the eighth subgroup of the Periodic Table of the Elements by Mendeleev. Preferred are the metals ruthenium, rhodium, palladium, platinum, cobalt and nickel and compounds thereof. The metal compounds may be, for example, chlorides, oxides, hydroxides and/or oxyhydrates.

The metals copper, vanadium, molybdenum, chromium and/or manganese, and compounds of these metals, can additionally be present.

The hydrogenation catalysts can consist exclusively or mostly of hydrogen-transferring substances, but these can also be fixed to support materials.

Suitable examples for support materials for the hydrogen-transferring substances are: inorganic materials, such as kieselguhr, silica, alumina, alkali metal silicates and alkaline earth metal silicates, aluminium silicates, montmorillonite, zeolite, spinells, dolomite, kaolin, magnesium silicates, zirconium oxide, zinc oxide, calcium carbonate, silicium carbide, aluminium phosphate, boron phosphate, asbestos, activated charcoal or barium sulphate, but also organic materials, for example naturally occurring or synthetic compounds having high molecular weights such as silk, polyamides, polystyrenes, cellulose or polyurethanes. Inorganic support materials in the form of powders are preferred.

Support catalysts of this type can generally contain 0.5 to 50% by weight, preferably 1 to 10% by weight, of the hydrogen-transferring substance, based on the total weight of the support catalyst. Here, the hydrogen-transferring substance can be distributed homogeneously in the support material, however, preferred catalysts are those where the hydrogen-transferring substance is substituted in their outer layer or on their surface. The preparation and shaping of the catalysts which can be used in process (c) can be carried out in a known manner (see, for example, Houben-Weyl, Methoden der organischen Chemie [Methods of Organic Chemistry], Volume IV, Ic, Part I, p. 16 to 26, Georg Thieme Verlag, Stuttgart, 1980).

Preferred support catalysts are ruthenium on charcoal, ruthenium on aluminium oxide, rhodium on charcoal, rhodium on aluminium oxide, palladium on charcoal, palladium on aluminium oxide, palladium on calcium carbonate, palladium on barium sulphate, palladium on silica, platinum on charcoal and platinum on aluminium oxide, nickel on kieselguhr, nickel on aluminium oxide and also nickel and palladium on aluminium oxide.

Preferred hydrogenation catalysts for hydrogenation in the heterogeneous system are those which consist exclusively or mostly of hydrogen-transferring substance, for example oxidic catalysts, such as palladium oxide, platinum oxide, ruthenium oxide and/or rhodium oxide/platinum oxide as described by Nishimura, furthermore black-based catalysts, such as palladium black, platinum black and rhodium black, which can be prepared by reducing corresponding metal salts or metal salt mixtures with alkali hydrides, alkali boranates, metal alkyls, hydrazine, formaldehyde, hydrogen or electropositive metals; and also skeletal catalysts of the Raney type, such as Raney nickel, Raney cobalt, Raney nickel/cobalt, Raney nickel/iron, Raney nickel/copper, Raney nickel/iron/chromium, Raney nickel/palladium and Raney nickel/iron/vanadium.

When the hydrogenation is carried out in the heterogeneous system, the hydrogenation catalysts are employed in step two of process (c) in an amount such that 0.05 to 2.5, preferably 0.1 to 1% by weight of hydrogen-transferring substance, based on the total weight of the reaction mixture, are present.

It is also possible to use mixtures of two or more of the hydrogenation catalysts mentioned for carrying out step two of process (c).

When carrying out step two of process (c), the catalytic activity of the hydrogenation catalysts is generally maintained to a large extent, so that they can be employed repeatedly when the hydrogenation is carried out batchwise and, when the hydrogenation is carried out continuously, can remain in use for a relatively long time.

The reaction temperatures in step two of process (c) can be varied within a relatively wide range. In general, the process is carried out between 0° C. and 150° C., preferably between 20° C. and 120° C.

The heterogeneously catalyzed hydrogenations in step two of process (c) are preferably carried out under increased pressure. In general, the process is carried out between 1 and 150 bar, preferably between 10 and 60 bar.

Besides the hydrogenation catalysts mentioned, of heterogeneous nature, it is also possible to employ homogeneously dissolved hydrogenation catalysts when carrying out step two of process (c). The selectivity of homogeneous hydrogenation catalysts is often higher compared with heterogeneous catalysts and permits selective hydrogenation of cyclopropyl ketones of the formula (XI) which contain additional substituents which can be hydrogenated or which are sensitive to hydrolysis, such as, for example, halogen on the phenyl radical. Examples of such homogeneous hydrogenation catalysts are complexes which contain the metals of the eighth subgroup of the Periodic Table of the Elements by Mendeleev as the central atom. The metals ruthenium, rhodium, palladium, iridium, cobalt and nickel are preferred. Ruthenium, rhodium and iridium are particularly preferred. Examples which may be mentioned of metal complexes of this type are tris-(triphenylphosphine)-rhodium(I) chloride, tris-(triphenylphosphine)-ruthenium(II) chlorideand bis-(triphenylphos-phine)carbonyl-iridium(I) chloride.

Suitable diluents for carrying out step two of process (c) are inert organic solvents when homogeneously dissolved hydrogenation catalysts are used. Alcohols, such as methanol, ethanol, isopropanol or ethylene glycol, furthermore hydrocarbons, such as toluene, moreover ketones, such as acetone and butanone, and also esters, such as ethyl acetate, can preferably be used.

When the hydrogenation is carried out in the homogeneous system, the hydrogenation catalysts for carrying out step two of process (c) are generally employed in an amount such that 0.01 to 2.5 mol %, preferably 0.05 to 1.0 mol %, of hydrogenation catalyst complex, based on cyclopropyl ketone employed of the formula (XI) are present.

When hydrogenation in the homogeneous system is carried out in step two of process (c), the reaction temperatures can also be varied within a relatively wide range. In general, the process is carried out at temperatures between 0° C. and 150° C., preferably between 20° C. and 120° C.

The hydrogenations, carried out in a homogeneous system, in step two of process (c) are preferably carried out under increased pressure. In general, the process is carried out under pressures between 1 and 150 bar, preferably between 10 and 100 bar.

In a variant, the hydrogenation in the homogeneous system in step two of process (c) can also be carried out in a way that hydrogenation is not carried out using molecular hydrogen but that reducing agents are employed which are capable of transferring one or more than one hydrogen atoms to the cyclopropyl ketone of the formula (XI), in the presence of a suitable catalyst, in the sense of a transfer hydrogenation, and thus act as hydrogen donors. In principle, possible catalysts for such a transfer hydrogenation are the complexes of metals of the eighth subgroup of the Periodic Table of the Elements by Mendeleev, which have already been described for the homogeneously catalyzed hydrogenation using molecular hydrogen in step two of process (c).

Suitable hydrogen donors in this process are primary and secondary, mono- or poly-hydric alcohols. Methanol, ethanol, n-propanol, i-propanol, n-butanol, 2-butanol, benzyl alcohol, ethylene glycol, 1,3-propanediol, 1,4-butanediol and 1,5-pentanediol can preferably be used. These alcohols can act both as hydrogen donors and as solvents.

Other hydrogen donors which can be employed in step two of process (c) are alkali metal salts and alkaline metal earth salts of formic acid, such as sodium formate and potassium formate, and also formic acid itself. When a salt of formic acid is used, step two of process (c) can be carried out in the form of a phase-transfer catalysis, the cyclopropyl ketone of the formula (XI) and the hydrogenation catalyst being dissolved in a suitable inert solvent and the formate being present as an aqueous solution in a second phase. Suitable solvents in this connection are therefore those solvents which, on the one hand, dissolve the cyclopropyl ketone of the formula (XI) and the hydrogenation catalyst but, on the other hand, are water-immiscible. Examples of solvents of this type are benzene, toluene, chlorobenzene, dichlorobenzenes and methylene chloride. Suitable phase-transfer catalysts are all reaction accelerators which can be employed for this purpose in organic chemistry. Tetrabutyl-ammonium bromide and methyltridecylammonium chloride (Aliquat ® 336) can preferably be used.

The reaction time required in step two of process (c) is a function of the reaction temperature, the hydrogen partial pressure, the intensity of mixing the reaction mixture and of the activity and concentration of the hydrogenation catalyst. In general, the reaction time required is within the range of 15 minutes up to several hours. Working up is carried out in each case by customary methods.

The compounds of the formula (VIII) also required as starting substances in process (b) are generally known compounds of organic chemistry.

Suitable acid-binding agents for carrying out process (b) are all customary acid acceptors. Alkali metal carbonates and hydrogen carbonates, such as sodium carbonate, potassium carbonate or sodium hydrogen carbonate, furthermore alkali metal hydroxides and alkali metal alkoxides, such as sodium hydroxide, potassium hydroxide, sodium methoxide or potassium tert.-butoxide, furthermore tertiary aliphatic or aromatic amines, such as triethylamine, N,N-dimethyl-cyclohexyl-amine, N,N-dimethyl-benzylamine and pyridine, and also cyclic amines, such as 1,5-diaza-bicyclo[4.3.0]non-5-ene (DBN), 1,8-diaza-bicyclo[5.4.0]undec-7-ene (DBU) and 1,4-diaza-bicyclo[2.2.2]octane (DABCO) can preferably be used.

Suitable diluents for carrying out process (b) are all inert organic solvents. Aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as dimethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile and pyridine, and also strongly polar solvents, such as dimethylformamide and dimethyl sulphoxide, can preferably be used.

In process (b), the reaction temperatures can be varied within a relatively wide range. In general, the process is carried out at temperatures between 0° C. and 150° C., preferably between 20° C. and 130° C.

When carrying out process (b), 1 to 1.5 moles of compounds of the formula (VIII) and 1 to 2 moles of acid-binding agent are generally employed per mole of halogenoketone of the formula (VII). Working up is carried out by customary methods. In general, a procedure is followed in which, if appropriate after previously filtering off precipitated salts, the reaction mixture is concentrated, the residue is taken up in an organic solvent which is sparsely water-miscible, and the resulting solution is washed, dried and then concentrated.

Dimethyl-oxo-sulphonium methylide, of the formula (V) and required as reactant in process (a), is known (cf. J. Am. Chem Soc. 87, 1363-1364 (1965)). For the above reaction, it is used in the freshly prepared state, by preparing it in situ by reacting trimethyloxosulphonium iodide with sodium hydride or sodium amide, in particular with potassium tert.-butoxide or sodium methoxide, in the presence of a diluent.

Dimethylsulphonium methylide, of the formula (VI) and also suitable as a reactant in process (a), is likewise known (cf. Heterocycles 8, 397 (1977)). If appropriate, it is employed in the above reaction in the freshly prepared state, by preparing it in situ, for example from trimethylsulphonium halide or trimethylsulphonium methylsulphate, in the presence of a strong base, such as, for example, sodium hydride, sodium amide, sodium methoxide, potassium tert.-butoxide or potassium hydroxide, in the presence of a diluent, such as tert.-butanol or dimethyl sulphoxide.

Suitable diluents for carrying out process (a) are inert organic solvents. Alcohols, such as tert.-butanol, ethers, such as tetrahydrofuran or dioxane, furthermore aliphatic and aromatic hydrocarbons, such as benzene, toluene or xylene, and also strongly polar solvents, such as dimethyl sulphoxide, can preferably be used.

When carrying out process (a), the reaction temperatures can be varied within a relatively wide range. In general, the process is carried out between 0° C. and 100° C., preferably between 10° C. and 60° C.

When carrying out process (a), 1 to 3 moles of dimethyloxosulphonium methylide of the formula (V) or of dimethylsulphonium methylide of the formula (VI) are generally employed per mole of cyclopropyl ketone of the formula (IV). The oxiranes of the formula (II) are isolated by customary methods.

1,2,4-Triazole, of the formula (III) and required as reactant for carrying out the process according to the invention, is a generally known compound of organic chemistry.

Suitable acid-binding agents for carrying out the process according to the invention are all customary acid acceptors. Alkali metal carbonates and hydrogen carbonates, such as sodium carbonate, potassium carbonate or sodium hydrogen carbonate, furthermore alkali metal hydroxides and alkali metal alkoxides, such as sodium hydroxide, potassium hydroxide, sodium methoxide or potassium tert.-butoxide, furthermore tertiary aliphatic or aromatic amines, such as triethylamine, N,N-dimethylcyclohexyl-amine, N,N-dimethylbenzylamine and pyridine, and furthermore cyclic amines, such as 1,5-diaza-bicyclo[4.3.0]non-5-ene (DBN), 1,8-diaza-bicyclo[5.4.0]undec-7-ene (DBU) and 1,4-diaza-bicyclo[2.2.2]octane (DABCO) can preferably be used.

Suitable diluents for carrying out the process according to the invention are all customary inert organic solvents. Nitriles, such as in particular acetonitrile; aromatic hydrocarbons, such as benzene, toluene and dichlorobenzene; formamides, such as in particular dimethylformamide, and also hexamethylphosphoric triamide, can preferably be used.

When carrying out the process according to the invention, the reaction temperatures can be varied within a relatively wide range. In general, the process is carried out at temperatures between 0° C. and 200° C., preferably between 50° and 150° C.

When carrying out the process according to the invention, 1 to 4 moles of 1,2,4-triazole of the formula (III) and 1 to 2 moles of a base are preferably employed per mole of oxirane of the formula (II). The end products are isolated in a customary manner.

The substances of the formula (I), which can be obtained by the process according to the invention, can be converted into acid addition salts or metal salt complexes.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering off, and, if appropriate, purified by washing with an inert organic solvent.

Suitable salts for the preparation of metal salt complexes of the compounds of the formula (I) are preferably those of metals which have already been mentioned in connection with the description of the metal salt complexes according to the invention as being preferred metal salts.

The metal salt complexes of the compounds of the formula (I) can be obtained in a simple manner by customary processes, thus, for example, by dissolving the metal salt in alcohol, for example ethanol, and adding the solution to compounds of the formula (I). Metal salt complexes can be isolated in a known manner, for example by filtering off, and, if appropriate, they can be purified by recrystallization.

The active compounds according to the invention exhibit a powerful microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, *Xanthomonas campestris pv. oryzae*; Pseudomonas species, such as, for example, *Pseudomonas syringae pv. lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal diseases, such as *Erysiphe graminis, Puccinia recondita, Cochliobolus sativus, Pyrenophora teres, Leptosphaeria nodorum* and barley mildew; furthermore rice diseases, such as *Pyricularia oryzae* and *Pellicularia sasakii*; and also Venturia species and cucumber mildew. Moreover, the substances have a very good in-vitro action.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

The amount of application in the use forms can be varied within a substantial range. The active compound concentrations are in the treatment of parts of plants in the use forms, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and the use of the active substances according to the invention can be seen from the examples below.

PREPARATION EXAMPLES

EXAMPLE 1

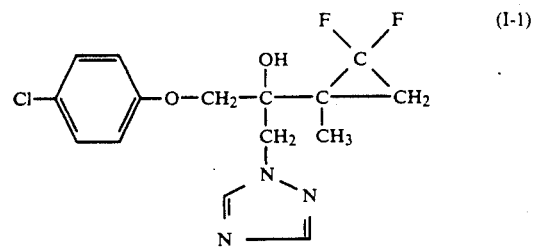

4.2 g (0.015 mol) of 2-(4-chlorophenoxymethyl)-2-(2,2-difluoro-1-methylcyclopropyl)-oxirane, 2.1 g (0.03 mol) of 1,2,4-triazole and 4.2 g (0.03 mol) of potassium carbonate are stirred for 16 hours at 90° C. in 30 ml of dimethylformamide. After the solvent has been removed using an oilpump, the residue is stirred with water/methylene chloride, and the organic phase is separated off and concentrated. The residue is purified by means of column chromatography (chloroform-/ethyl acetate=4:1) on silica gel.

2.3 g (44.6% of theory) of 1-(4-chlorophenoxy)-2-(2,2-difluoro-1-methylcyclopropyl)-2-hydroxy-3-(1,2,4-triazol-1-yl)-propane of melting point 110° C. are obtained.

Preparation of starting substances

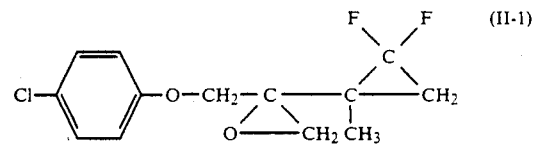

2.4 g (0.044 mol) of sodium methoxide are added to the solution of 30 ml (0.04 mol) of a 1.36-molar solution of trimethylsulphonium methylsulphate in acetonitrile, and the mixture is stirred at room temperature for 30 minutes. 5.8 g (0.022 mol) of 1-(4-chlorophenoxyacetyl)-1-methyl-2,2-difluorocyclopropane are then added, and the mixture is stirred for 16 hours at 20° C. The reaction mixture is poured into 200 ml of water and extracted using methylene chloride, and the organic phase is washed with water and concentrated. 4.3 g (GC content of 73%; 71.6% of theory) of 2-(4-chlorophenoxymethyl)-2-(2,2-difluoro-1-methylcyclopropyl)-oxirane are obtained as a viscous resin which is reacted further directly.

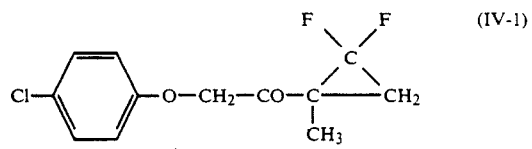

6 g (0.028 mol) of 1-bromoacetyl-1-methyl-2,2-difluorocyclopropane are refluxed for 16 hours in 30 ml of acetone with the addition of 4.4 g (0.032 mol) of potassium carbonate and 4.1 g (0.032 mol) of 4-chlorophenol, with stirring. The mixture is diluted with water, the product is extracted using methylene chloride, and the organic phase is washed once using dilute sodium hydroxide solution and then water and concentrated under reduced pressure.

6 g of 1-(4-chlorophenoxyacetyl)-1-methyl-2,2-difluorocyclopropane are obtained as a crude product of a content (GC) of 66% (54.4% of theory).

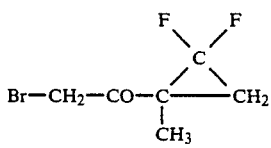
(VII-1)

A solution of 4.7 ml (0.09 mol) of bromine in 30 ml of methylene chloride is added dropwise at 20° C. to the stirred solution of 12.5 g (0.09 mol) of 1-acetyl-1-methyl-2,2-difluoro-cyclopropane in 50 ml of methanol. When decolouration is complete, the reaction mixture is poured into 200 ml of water and extracted with methylene chloride. After concentrating the mixture under reduced pressure, 20 g (GC content 47%; 47% of theory) of crude 1-bromoacetyl-1-methyl-2,2-difluorocyclopropane, which is reacted directly without further purification, are obtained.

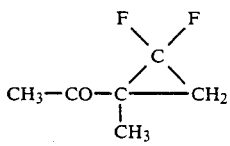
(X-1)

333 ml of a 1.5-molar methyllithium solution (0.5 mol) are added dropwise at −78° C. under nitrogen with stirring to 34 g (0.25 mol) of 2,2-difluoro-1-methylcyclopropane carboxylic acid in 250 ml of dry diethyl ether. Stirring is continued for one hour at −78° C., and the reaction solution is then warmed at 0° C. and poured onto 500 g of ice and 50 ml of concentrated hydrochloric acid. The organic phase is separated off and the aqueous phase is extracted using ether. The combined organic phases are dried over sodium sulphate, the solvent is distilled off, and the product is distilled under slightly reduced pressure.

21 g (63% of theory) of 2,2-difluoro-1-methylcyclopropyl methyl ketone of boiling point 58°–60° C./60 mbar are obtained.

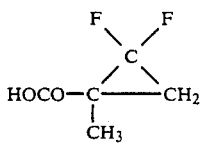
(XIII-1)

2.3 kg (14.47 mol) of potassium permanganate are added in portions to 840 g (7.12 mol) of 2,2-difluoro-1-methyl-1-vinyl-cyclopropane in 10 l of water. The mixture is stirred at room temperature for 36 hours, and manganese oxide is filtered off and rinsed thoroughly with water. The filtrate is acidified using concentrated hydrochloric acid and extracted using dichloromethane. After the organic phase has been dried, the solvent is removed under reduced pressure and the residue is distilled.

In this way, 750 g (77% of theory) of 2,2-difluoro-1-methylcyclopropanecarboxylic acid (77% of theory) of melting point 59°–61° C. are obtained.

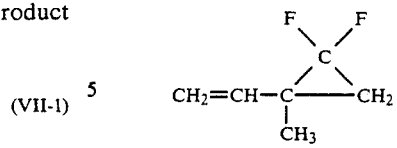
(XII-1)

The addition of difluorocarbene onto isoprene with the formation of 2,2-difluoro-1-methyl-1-vinyl-cyclopropane is already known and has been described by M. Kamel, W. Kimpenhaus, J. Buddrus, Chem. Ber. 109, 2351 (1976).

EXAMPLE 2

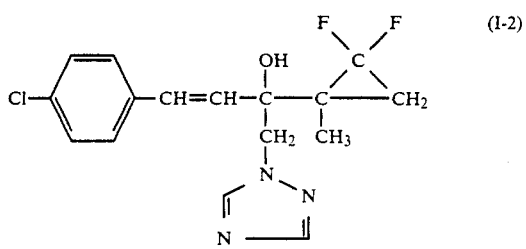
(I-2)

1.4 g (0.048 mol) of 80% strength sodium hydride is added in portions to the solution of 3.3 g (0.048 mol) of 1,2,4-triazole in 30 ml of dimethylformamide, and the mixture is stirred for 30 minutes at 20°–30° C. 6.6 g (0.024 mol) of 2-(2,2-difluoro-1-methyl-cyclopropyl)-2-[2-(4-chlorophenyl)-ethen-1-yl]-oxirane are subsequently added, and the mixture is stirred at 90° C. for 16 hours. The reaction mixture is then poured into water and extracted using methylene chloride, the organic phase is concentrated under reduced pressure, and the residue is purified by chromatography on silica gel (chloroform/ethyl acetate=4:1).

2.4 g (29.6% of theory) of 1-(4-chlorophenyl)-3-(2,2-difluoro-1-methylcyclopropyl)-3-hydroxy-4-(1,2,4-triazol-1-yl)-but-1-ene of melting point 131° C. are obtained.

Preparation of starting substances

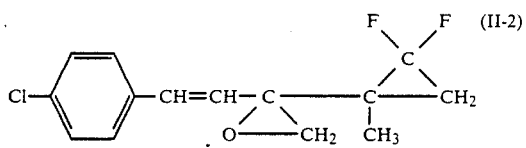
(II-2)

3.6 g (0.066 mol) of sodium methoxide are added to 41 ml (0.06 mol) of a 1.46-molar solution of trimethylsulphonium methylsulphate in acetonitrile, and the mixture is stirred at room temperature for 30 minutes. A solution of 10 g (0.039 mol) of 2,2-difluoro-1-methyl-cyclopropyl [(2-(4-chlorophenyl)-ethen-1-yl] ketone in 100 ml of acetonitrile is subsequently added, and the mixture is stirred for 16 hours at room temperature. The reaction mixture is poured into water and extracted using methylene chloride, and the organic phase is washed twice with water and concentrated under reduced pressure.

6.8 g (GC content 38%; 24% of theory) of 2-(2,2-difluoro-1-methylcyclopropyl-2-[2-(4-chlorophenyl)-ethen-1-yl]-oxirane which is reacted directly without further purification, are obtained.

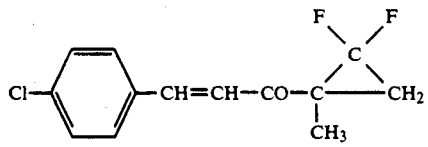
(IV-2)

A solution of 15.5 g (0.11 mol) of p-chlorobenzaldehyde in 20 ml of methanol is added at 20° C. to 15 g (0.11 mol) of 1-acetyl-2,2-difluoro-1-methylcyclopropane in 20 ml of 10% strength methanolic sodium hydroxide solution, with stirring. After 15 minutes, 40 more milliliters of 10% strength methanolic sodium hydroxide solution are added and the mixture is stirred at room temperature for 16 more hours. The reaction mixture is poured into water and extracted with methylene chloride, and the organic phase is washed with water and concentrated under reduced pressure.

25 g (88% of theory) of crude 2,2-difluoro-1-methylcyclopropyl [2-(4-chlorophenyl)-ethen-1-yl]-ketone are obtained as an oil which is directly reacted further.

The substances listed in Table 2 below are obtained correspondingly to Examples 1 and 2 and in accordance with the process conditions indicated:

TABLE 2 (I)

| Compound No. | Ar | Y | R | $X^1$ | $X^2$ | Physical Constant m.p. (°C.) |
|---|---|---|---|---|---|---|
| I-3 | F₃CO—⟨phenyl⟩— | —OCH₂— | CH₃ | F | F | resin |
| I-4 | 2,4-dichlorophenyl | —OCH₂— | CH₃ | F | F | resin |
| I-5 | Cl—⟨phenyl⟩— | —CH₂CH₂— | CH₃ | F | F | 112 |
| I-6 | 3,4-difluorophenyl | —OCH₂— | CH₃ | F | F | resin |
| I-7 | 2-fluorophenyl | —OCH₂— | CH₃ | F | F | resin |
| I-8 | 4-chloro-2-methylphenyl | —OCH₂— | CH₃ | F | F | resin |
| I-9 | Cl—⟨phenyl⟩— | —OCH₂— | CH₃ | Cl | Cl | resin |

TABLE 2-continued $$Ar-Y-\underset{\underset{\underset{N\diagdown N}{\overset{|}{CH_2}}}{\overset{OH}{|}}}{C}-\underset{R}{\overset{X^1}{\underset{|}{C}}}\underset{CH_2}{\overset{X^2}{\diagup}}C \quad (I)$$

| Compound No. | Ar | Y | R | X¹ | X² | Physical Constant m.p. (°C.) |
|---|---|---|---|---|---|---|
| I-10 | 4-Cl-C₆H₄- | —CH₂CH₂— | CH₃ | Cl | Cl | 109–112 |
| I-11 | CH₃—O—N=CH—C₆H₄- | —OCH₂— | CH₃ | F | F | resin |
| I-12 | 4-F-C₆H₄- | —OCH₂— | CH₃ | F | F | resin |
| I-13 | 2,4-Cl₂-C₆H₃- | —CH=CH— | CH₃ | F | F | resin |

In the following use examples, the compounds of the formulae indicated below were employed as comparison substances:

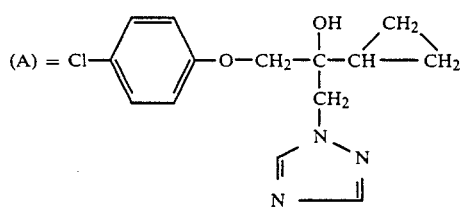

(A) =

(disclosed in EP-OS (European Published Specification) 0,040,345)

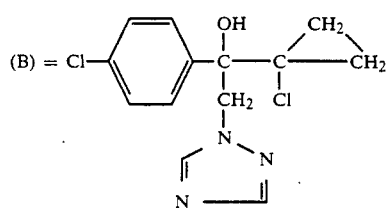

(B) =

(disclosed in EP-OS (European Published Specification) (0,180,136)

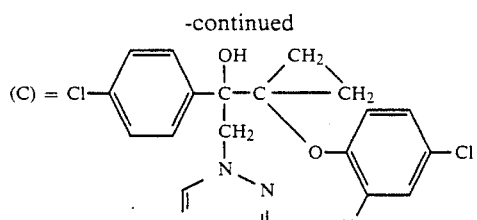

(C) =

(disclosed in EP-OS (European Published Specification) 0,180,136)

EXAMPLE A

Erysiphe Test (Wheat)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. tritici.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds according to the invention (I-1), (I-2), (I-3) and (I-4) show a considerably better activity than comparison substances (B) and (C).

EXAMPLE B

Puccinia Test (Wheat)/Protective

Solvent: 100 parts by weight of dimethylformamide
Emulsifier: 0.025 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabin at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, the compounds according to the invention (I-1), (I-2), (I-3), (I-4) and (I-5) show a considerably better activity than comparison substance (A).

EXAMPLE C

Venturia Test (Apple)/Protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia in a equal is) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compounds according to the invention (I-1), (I-2) and (I-5) show a considerably better activity than comparison substance (C).

It is understood that the specification and examples are illustrative but not limitative of the present invention and that other embodiments within the spirit and scope of the invention will suggest themselves to those skilled in the art.

What is claimed is:

1. A 2,2-dihalogenocyclopropyl-hydroxyethyl-triazole of the formula $$\text{Ar}-Y-\underset{\underset{\underset{N \diagup\diagdown N}{\|}}{\underset{CH_2}{|}}}{\overset{OH}{\underset{|}{C}}}-\underset{\underset{CH_3}{|}}{C}-\overset{X^1 \diagup X^2}{\underset{\diagdown CH_2}{C}} \quad (I)$$

in which
Ar represents phenyl which can be mono- or disubstituted by identical or different substituents selected from the group consisting of fluorine, chlorine, methyl, trifluoromethoxy and methoximinomethyl,
$X^1$ represents fluorine or chlorine,
$X^2$ represents fluorine or chlorine and
Y represents the groups $-OCH_2-$, $-SCH_2-$, $-CH_2CH_2-$ or $-CH=CH-$, where the hetero atom is linked to the aryl radical when Y represents $-OCH_2-$.

2. A 2,2-dihalogenocyclopropyl-hydroxyethyl-triazole according to claim 1, wherein such compound is 1-(4-chlorophenoxy)-2-(2,2-difluoro-1-methylcyclopropyl)-2-hydroxy-3-(1,2,4-triazol-1-yl)-propane of the formula 3. A compound according to claim 1, wherein such compound is 1-(4-chlorophenyl)-3-(2,2-difluoro-1-methylcyclopropyl)-3-hydroxy-4-(1,2,4-triazol-1-yl)-but-1-ene of the formula:

4. A compound according to claim 1, wherein such compound is 1-(4-chlorophenyl)-3-(2,2-difluoro-1-methylcyclopropyl)-3-hydroxy-4-(1,2,4-triazol-1-yl)-butane of the formula

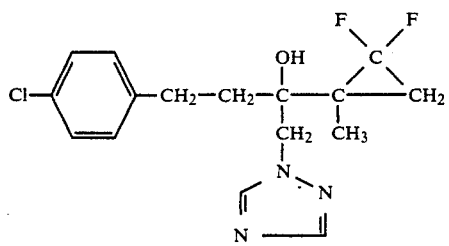

5. A fungicidal composition comprising a fungicidally effective amount of a compound or addition product according to claim 1 and an inert diluent.

6. A method of combating fungi which comprises applying to such fungi or to a fungus habitat an amount effective therefor of a compound or addition product according to claim 1.

7. The method according to claim 6, wherein such compound is
1-(4-chlorophenoxy)-2-(2,2-difluoro-1-methyl-cyclopropyl)-2-hydroxy-3-(1,2,4-triazol-1-yl)propane,
1-(4-chlorophenyl)-3-(2,2-difluoro-1-methyl-cyclopropyl)-3-hydroxy-4-(1,2,4-triazol-1-yl)-but-1-ene or
1-(4-chlorophenyl)-3-(2,2-difluoro-1-methyl-cyclopropyl)-3-hydroxy-4-(1,2,4-triazol-1-yl)-butane.

* * * * *